United States Patent [19]
Sedaros

[11] Patent Number: 6,004,259
[45] Date of Patent: Dec. 21, 1999

[54] BABY CALMER KIT USING MOTHER'S HEARTBEAT SOUND

[76] Inventor: Shawky Sedaros, 25 E. Silver Palm Ave., Melbourne, Fla. 32901

[21] Appl. No.: 08/852,465

[22] Filed: May 7, 1997

Related U.S. Application Data

[63] Continuation-in-part of application No. 08/307,312, Dec. 2, 1994, abandoned.

[51] Int. Cl.$^6$ .................................................. A61M 21/00
[52] U.S. Cl. .............................................................. 600/28
[58] Field of Search ......................................... 600/26–28

[56] References Cited

U.S. PATENT DOCUMENTS

| 3,292,610 | 12/1966 | Neuman ..................................... | 600/27 |
| 3,888,233 | 6/1975 | Ware ......................................... | 600/27 |
| 4,941,453 | 7/1990 | Shakas et al. ............................. | 600/28 |
| 5,063,912 | 11/1991 | Hughes ..................................... | 600/28 |
| 5,205,811 | 4/1993 | Fornarelli ................................. | 600/27 |

Primary Examiner—John P. Lacyk

[57] ABSTRACT

The object of this invention is to make life easier for the newborn parents. Heartbeat sound is known to produce a calming and soothing effect particularly when it is the mother's identical heartbeat which the infant came to know during gestation. Mothers, in general, prefer that their newborn listen to their own heartbeat, sound recognized by the infant, and not a composite of several ones as used in Hughes', mores, to an artificial or simulated heartbeat as described by numerous inventions. This invention provides a practical method for the mother to record her own heartbeat, which is played back by a device automatically activated by the crying of the baby. The object is to lure the baby into believing that his/her mother is present when needed based on hearing comforting familiar heartbeat even though she is not physically present. The recorded mother's heartbeat is achieved by the use of a stethoscope fitted with a diaphragm in one end of the acoustical tube and the other end plugs in a microphone record of the device. The mother may rep eat her recording to obtain best results. The parent will place the device besides the crib, on standby mode, the sound is played back activated by the crying of the baby and remains activated until a pre-determined time interval of about 6 minutes after the crying has stopped. Continuous playback may be obtained by switching On S1, in FIG. 1a. Periodical checkings on the newborn are strongly suggested.

1 Claim, 5 Drawing Sheets

BLOCK DIAGRAM OVERVIEW

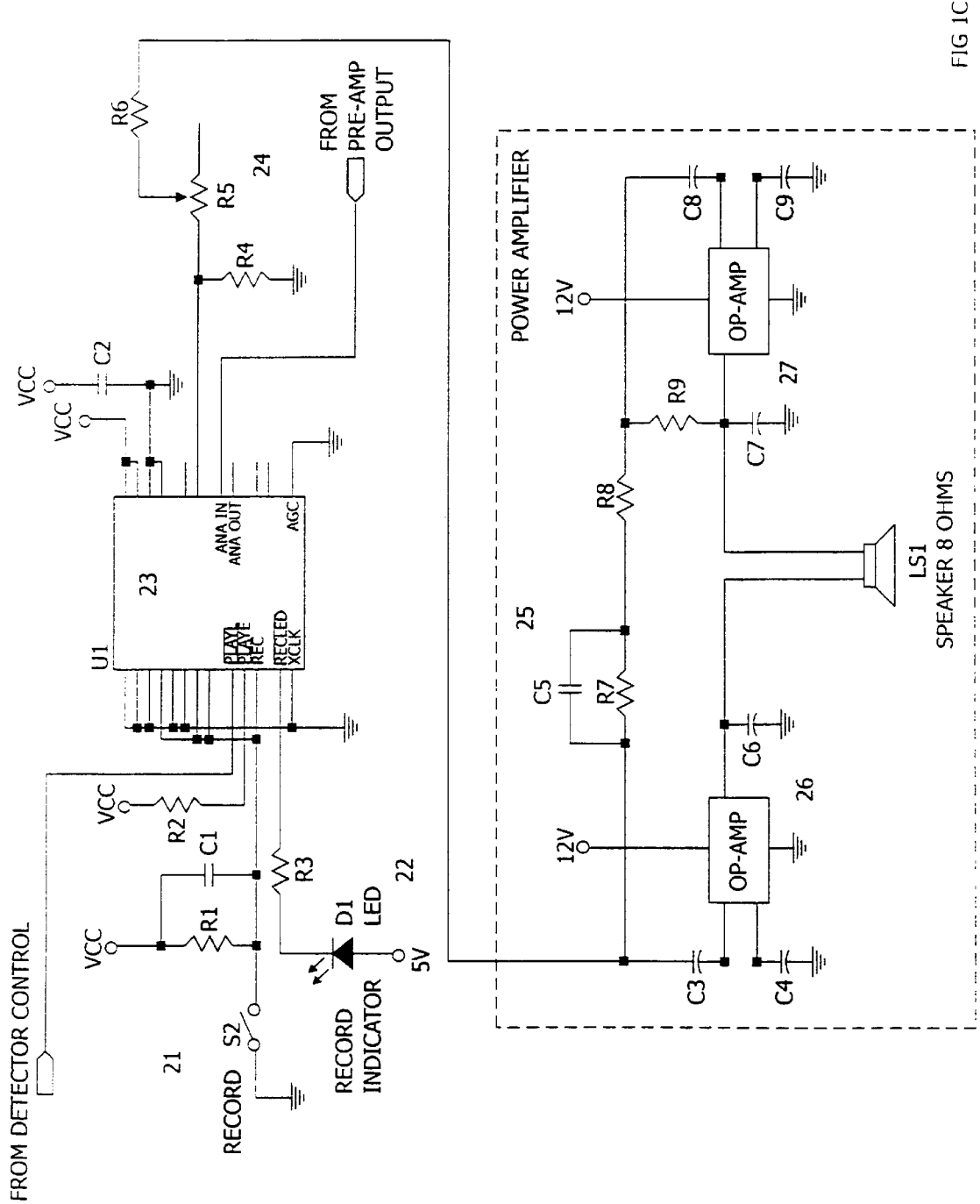

BABY CALMER KIT USING MOTHER'S HEARTBEAT SOUND

This is a continuation-in-part of application Ser. No. 08/307,312 filed in Dec. 02, 1994, now abandoned.

BACKGROUND OF THE INVENTION

This invention related to a special device that enables the mother to record her own heartbeat on a memory device which in turn played back activated by the crying of her baby, or by a noise loud enough to, awaken the newborn, which serves as a calmer and soother sound to sleep. This device is placed safely beside the crib.

(1) Field of the Invention

Infants recognize their own mother's heartbeat. This sound becomes a great comfort, to a stressed baby only second to the mother's holding and cuddling. Thus, true mother's heartbeat sound becomes a very effective way for calming and soothing a crying infant to sleep.

(2) Description of the Prior Art

Several devices were made to simulate the heartbeat and sleep inducing effect to newborn babies, among them U.S. Pat. No. 5,205,811 which provides a heartbeat simulator in a baby blanket pressure activated; and U.S. Pat. No. 3,888,233 which provides a figure with simulated heartbeat. U.S. Pat. No. 5,603,912 by Hughes mentions that "he had a womb sounds, including the heartbeat developed for him by inserting a microphone into a large number of wombs. An average sound was obtained then produced a composite sound by referring the former to the original sounds". No defined method was described in the invention to obtain the average and the composite sounds such as heartbeat, pulse rate, and the other womb sounds. Playback is also pressure activated; U.S. Pat. No. 3,2,92,610 describes an animated doll equipped with a transducer in the form of a combination of recording and sound reproducing appliance, a record player; this is used to distract the infant, or the child, to sleep.

SUMMARY OF THE INVENTION

A Sound Activated device, placed on a table near the crib, triggered by the crying of the infant by playing back the heartbeat, recorded earlier by the mother using a stethoscope with the ear piece removed from the acoustical tube to fit around a microphone coupled to a high fidelity recording circuit, connected to a voice integrated circuit specially wired for looping playback from address 0 and deleting the end of message marker the playback of the heartbeat is to start with the baby crying and to stop about 6 minutes after the crying has stopped. This will reassure the newborn by producing a calming and soothing effect, thus inciting the baby to go back to sleep.the advantages of this invention are: 1 it enables the mother to record her heartbeat in her own privacy which is not provided by Hughes that provides only a playback of an average womb sounds of several pregnant women recorded by inserting a microphone into their wombs; 2, a device that is activated by the crying of the newborn, or any other sound loud enough to awaken the baby, to playback the true mother's heartbeat thus producing a reassuring and calming effect thus inciting the infant to return to sleep. Continuous playback may be done manually for other applications.

These two options are not available in any of the references cited above.

BRIEF DESCRIPTION OF THE DRAWINGS

FIG. 1b, shows the recording circuit. A microphone and a 2 Stage Low Frequency Pre-Amplifier with a circuit to isolate the ripple effect from the microphone. It also shows the power supply with a filter to reduce the ripples from the power supply and a 5 V regulator that supply the VCC to the circuit shown in FIG. 1a.

FIG. 1c, shows the part of the recording circuit together with the speech IC wiring including the volume control and the playback circuit.

DESCRIPTION OF THE PREFERRED EMBODIMENT

Figure 1A:
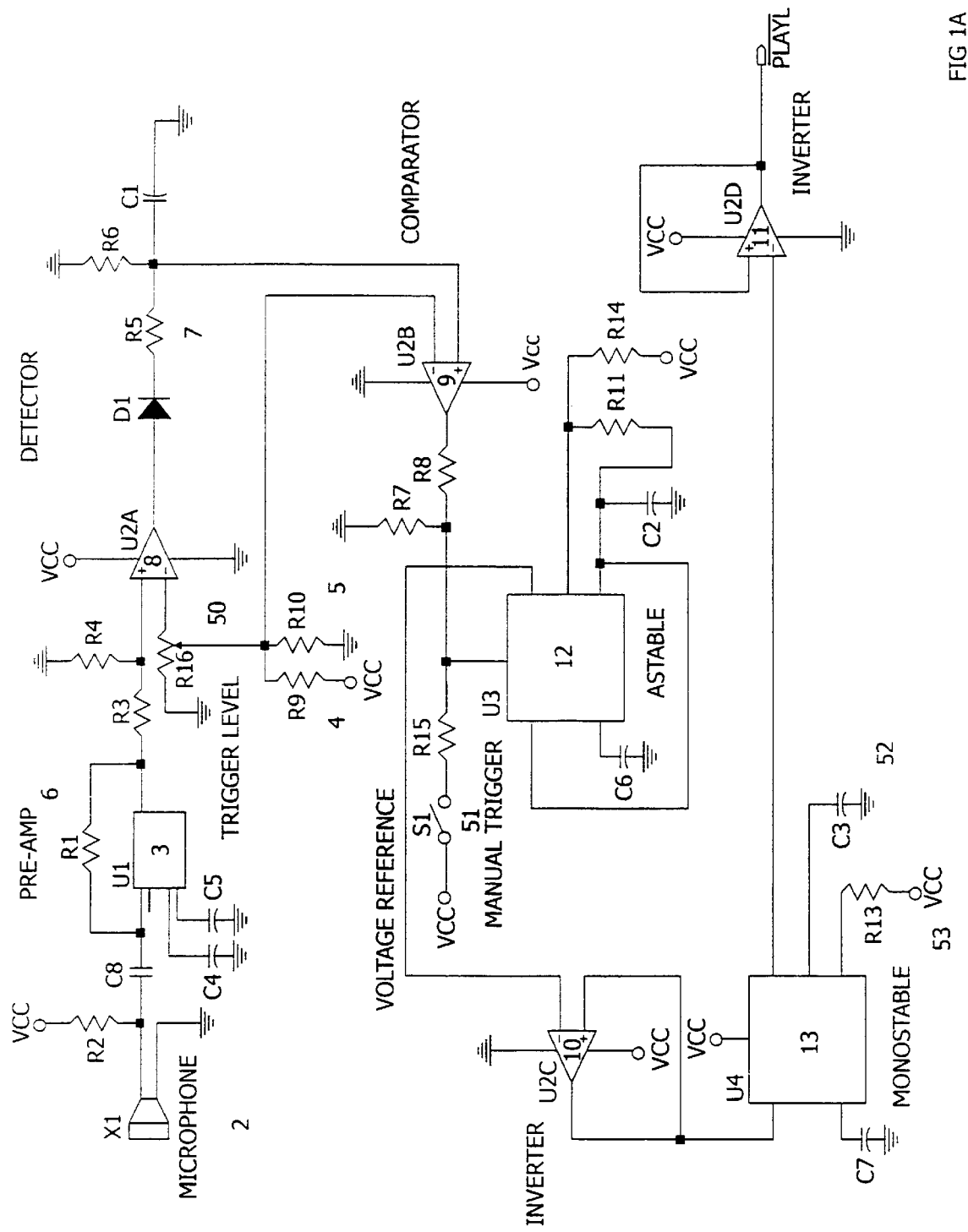
FIG. 1a, shows the noise detector called the sensor and playback time control part of the device.

FIG. 1a, referred to as numeral 1 shows a preferred form in circuit diagram of the section that detects the noise and controls the playback time slice. Numeral 2 shows an omnidirectional microphone to pickup the environment noise then amplified by 3 MC 34119, R1 numerical 6 a feedback that controls the gain of the Pre-amplifier 3. Numeral 4 & 50 R9, R10 provide a voltage reference of 2.5 V dc to the amplifier numeral 8 in the detector circuit 7. The trigger level control is factory set by a potentiometer R16 numeral 5'. The DC output from 8 is fed to the comparator numeral 9 that is also supplied with the reference voltage, both are parts of the IC UA3403 not shown in the diagram. The output is then fed to a timer LM555 numeral 12 working in an astable state, then to an inverter 10 part of IC UA3403 whose output serves to activate the monostable counter LM555 numeral 13. The time duration that activates the PLAYL\ in the speech IC, through the inverter 10 also part of IC UA3403, that requires a logic low to playback, is set by the time constant C3xR13 numeral 52' and 53' to about 6 minutes regardless to its input. If the baby's crying persists, the series of pulses generated by the astable counter 12 through the inverter 10 will reactivate counter 13 at the end of its time constant for another 6 minutes; and this will go on for 6 minutes after the crying has stopped.

Figure 1B:
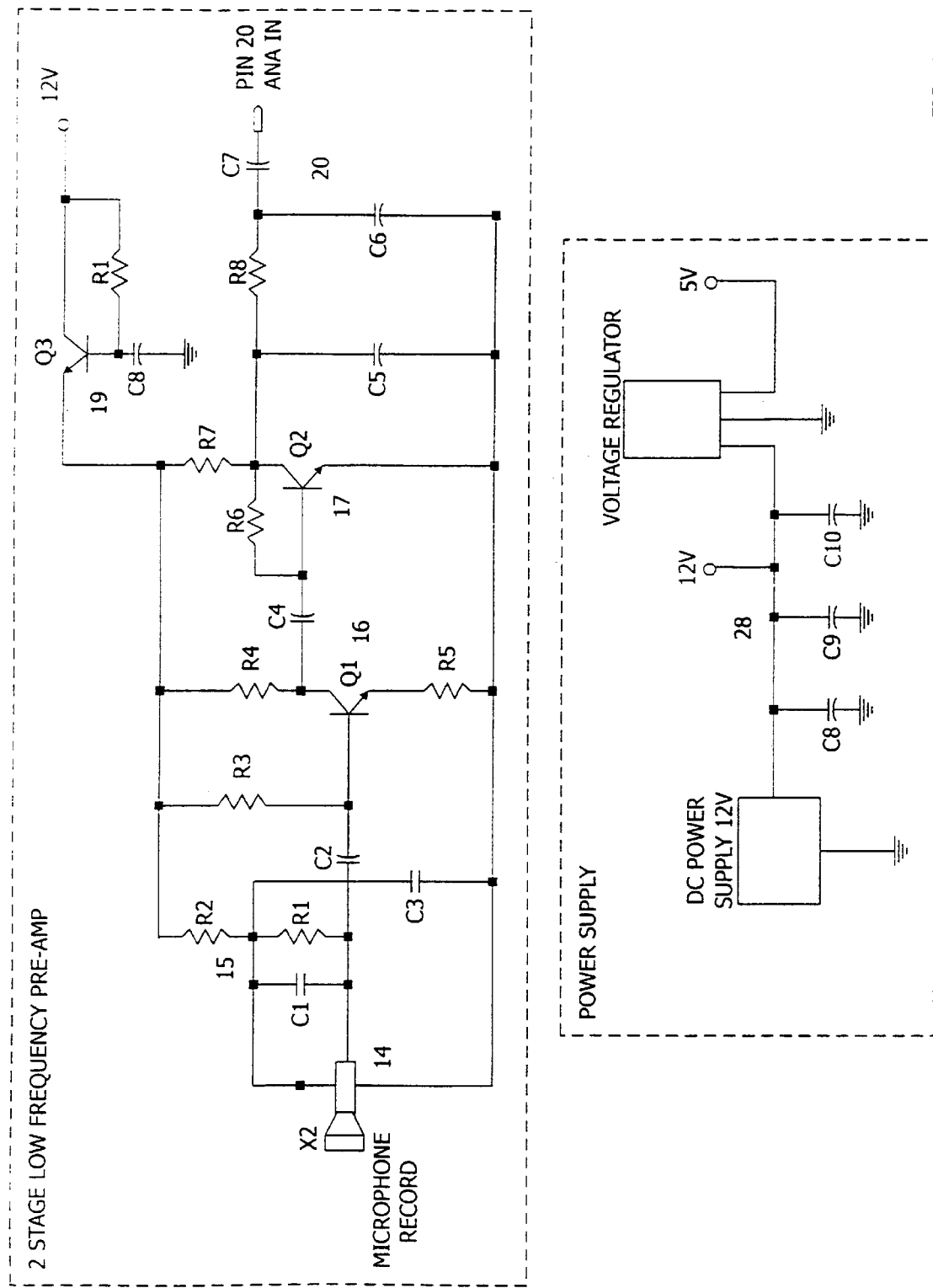

A switch S1 12' for manual control, if left on the On mode, the playback will be continuous, on the other hand, if switched On and back Off it will reset the circuit to playback for 6 minutes then stops in the absence of noise above the trigger level. FIG. 1b shows the recording circuit diagram together with the power supply. A directional microphone numeral 14, around which fits the free end of the acoustical tube 32 in FIG. 2 when recording, followed by a low frequency filter 14; the object is to record a low frequency weak signal with the highest possible S/N. A low pass filter 15 is to eliminate high frequency noise. A two stage low noise amplifiers 16 and 17 followed by a second low pass filter 20 then the signal is then coupled to ANA IN the Speech chip 23 in FIG. 1c. The circuit is supplied with a 12 V power through Q3 19; its function is to eliminate noise from the power supply to get to the microphone and the 2 Stage Pre-amplifier. The power supply circuit shows a 12 V DC power supply followed by a filter 28 where the supply 12 V is provided then, to a voltage regulator IC 7805 to provide the 5 V needed for VCC in FIG. 1a, and the speech circuit in FIG. 1c.

FIG. 1c, shows the wiring of the speech IC 23 to provide playback looping and suppression of EOM end of message marker, it also shows the connections from the Control circuit output from FIG. 1a and, the audio output from the Pre-Amplifier in FIG. 1b. A recording switch S2 21 to be on the ON mode while recording and a record indicator LED D1 22 will be lit indicating that recording is in progress and will remain ON for about 20 seconds duration. The speaker output is connected to an 8 ohm speaker through a volume control 24 followed by 2 Op-amplifiers 26 and 27 with a low pass filter 25. Pre-amplifiers within the speech IC are not used.

Figure 1D:
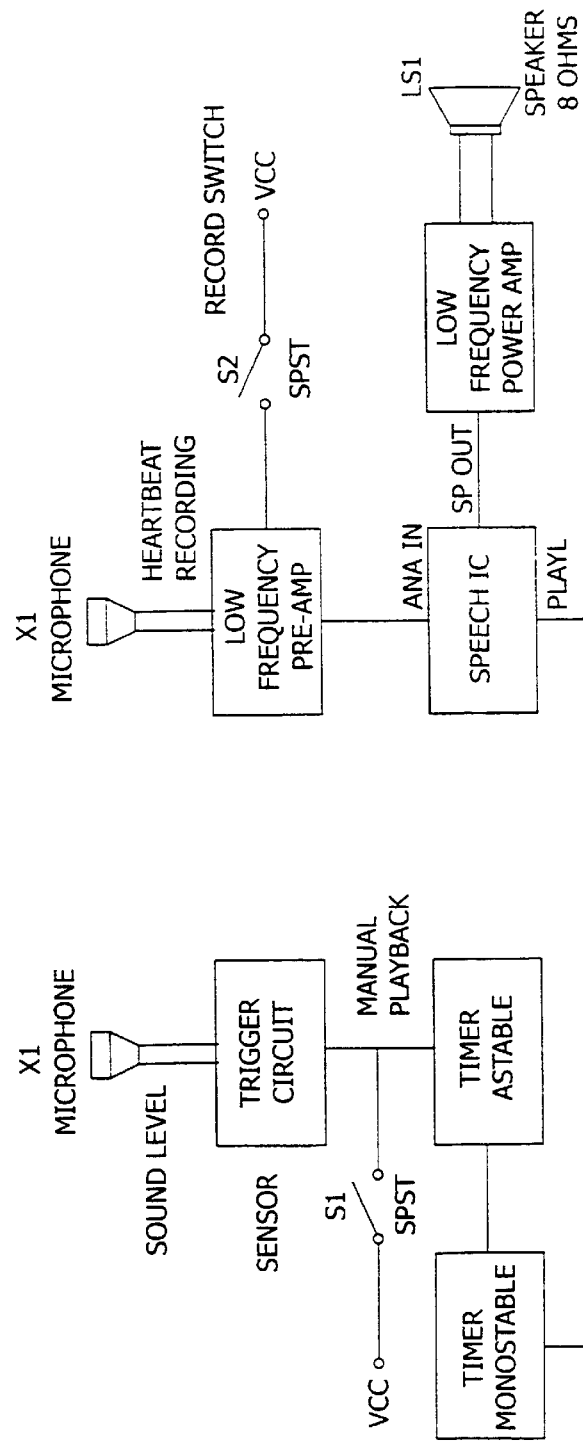
FIG. 1d, shows an accessory to the device in which a Block Diagram overview of FIG. 1a, 1band 1c.
Figure 2:
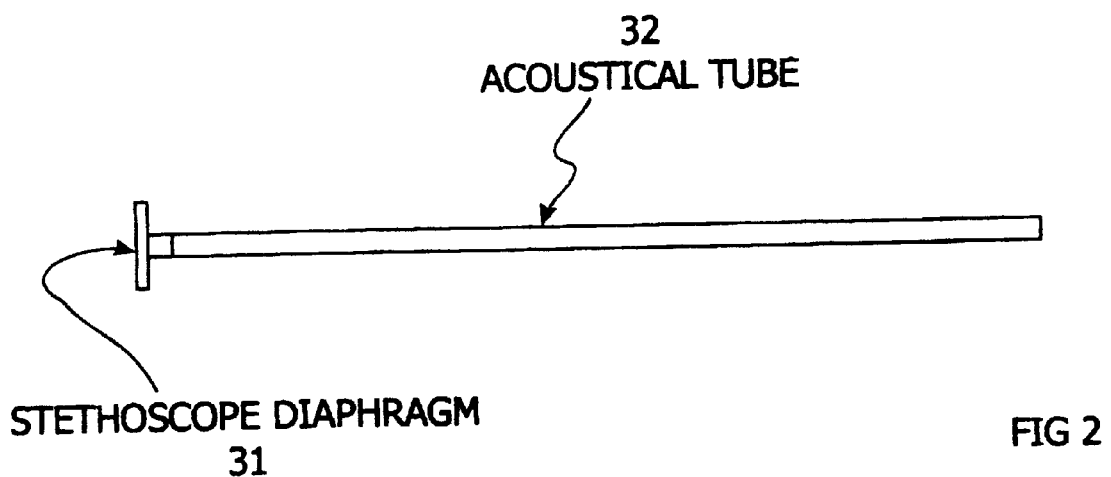
FIG. 2, shows a stethoscope with a diaphragm fitted in the acoustical tube in one end and the other end, the ear piece has been removed, to fit around the recording microphone.
Figure 3:
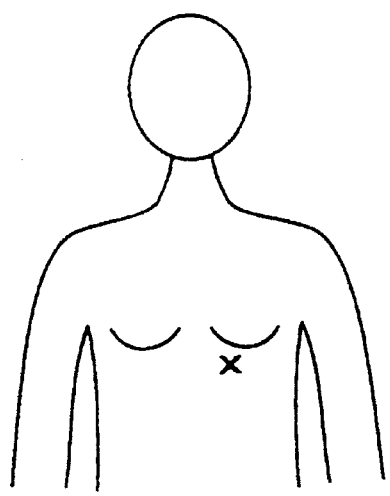
FIG. 3, shows a sketch with a mark to guide the mother to the spot where to place the microphone.

FIG. 1d, is a self explanatory block diagram combining all FIGS. 1a, 1b and 1c. FIG. 2, numerical 30 shows an accessory only used for recording; composed of a stethoscope diaphragm plugged into one end of an acoustical tubing FIG. 3, numeral 40 is a sketch with a mark to guide the mother to the spot where to place during recording.

While there is shown what is considered to be the preferred embodiments, it will be obvious to those skilled in the art that various changes and modifications, subject to performance and cost may be, brought without departing from the main scope of the invention.

Recording and Playback the Mothers Heartbeat

To record the heartbeat, the device referred as in FIG. 1d should be connected to the power supply. Plug the free end of the acoustical tube referred as in numerical 33 to the Microphone record 14 in FIG. 1b; then the mother may hold steadily the diaphragm of the stethoscope directly on her skin on the spot shown in numerical 40. Pull to On the recording switch numeral S2 number 21, in FIG. 1c, a red light will appear, LED 22, indicating that recording is in progress, this will stay on until the end of the recording time 20 seconds; then the record switch will be set Off. The mother will activate the device to listen to her recording by switching the standby S1 51' in FIG. 1a. to ON and back OFF, playback will occur for about 6 minutes; left on ON position, the playback will be continuous. If not satisfied with the resulted sound, she may slightly reposition the diaphragm back and forth around the specified spot and repeat the recording and the playback until best result is reached.

A medical tape may be used to secure the stethoscope in place while recording to eliminate static sounds. The parent will then unplug the tube from the recording microphone and the power after finishing recording and put off the recording switch.

The Parent or the Sitter Will Unplug the Power When the Unit Is Not In Use for safety reasons.

Before retiring and after checking on the baby's needs, the parent will set the device to standby mode by plugging the power supply then turn the standby switch on ON mode then back OFF. This will trigger the playback and stops after 6 minutes in the absence of the crying noise. The device will be, placed safely near the newborn crib. If the baby cries, the playback will be activated and heard by the infant. It is set to continuously stay activated during the crying of the baby and to stop at predetermined time slice, about 6 minutes, after the baby has stopped crying.

Having described my invention, I claim:

1. A baby calmer kit comprising:
  a) a stethoscope diaphragm; an acoustical tubing having one end connected to said stethoscope diaphragm and one free end;
  b) a sensitive unidirectional microphone having means capable of receiving a mother's heartbeat through said free end of said acoustical tubing; a two stage low frequency amplifier for amplifying an output of said microphone;
  c) an IC speech chip for storing the output received from said microphone or said amplifier, said IC speech chip including playback terminals;
  d) a playback timing circuit comprised of an astable timer and a monostable timer, said timers setting a playback time of the output from said microphone or said amplifier;
  e) a sensor comprised of an onmdirectional microphone, a preamplifier circuit, and a detector circuit to activate said playback terminals of said IC speech chip, said sensor detecting crying of an infant and subsequently activating said playback terminals of said IC speech chip.

* * * * *